United States Patent
Liu (10) Patent No.: US 7,134,319 B2
(45) Date of Patent: Nov. 14, 2006

(54) ACOUSTIC WAVE SENSOR WITH REDUCED CONDENSATION AND RECOVERY TIME

(75) Inventor: James Z. Liu, Rockford, IL (US)

(73) Assignee: Honeywell International Inc., Morristown, NJ (US)

( * ) Notice: Subject to any disclaimer, the term of this patent is extended or adjusted under 35 U.S.C. 154(b) by 205 days.

(21) Appl. No.: 10/918,687

(22) Filed: Aug. 12, 2004

(65) Prior Publication Data

US 2006/0032290 A1 Feb. 16, 2006

(51) Int. Cl.
*G01N 29/22* (2006.01)
*H03H 9/25* (2006.01)

(52) U.S. Cl. .................. 73/31.06; 73/29.01; 73/29.05; 73/31.05; 73/335.02; 310/313 R; 310/313 B; 333/141; 333/150; 333/193

(58) Field of Classification Search ............... 73/29.01, 73/29.02, 29.05, 31.05, 31.06, 335.02–335.05; 333/141, 142, 150, 154, 157, 158, 186, 193; 367/189, 190; 310/313
See application file for complete search history.

(56) References Cited

U.S. PATENT DOCUMENTS

| | | | | |
|---|---|---|---|---|
| 3,512,400 | A * | 5/1970 | Lynnworth ................... 73/597 |
| 4,312,228 | A * | 1/1982 | Wohltjen ..................... 73/597 |
| 4,793,182 | A * | 12/1988 | Djorup ..................... 73/335.02 |
| 5,155,708 | A | 10/1992 | Bedi et al. ................... 367/152 |
| 5,221,871 | A * | 6/1993 | Fuchs et al. ............. 310/313 R |
| 5,235,235 | A * | 8/1993 | Martin et al. ........... 310/313 D |
| 5,365,770 | A | 11/1994 | Meitzler et al. ............ 73/24.06 |
| 5,571,944 | A * | 11/1996 | Pfeifer et al. .............. 73/24.04 |
| 5,795,993 | A * | 8/1998 | Pfeifer et al. .............. 73/24.01 |
| 5,821,425 | A | 10/1998 | Mariani et al. ............... 73/703 |
| 6,170,318 | B1 | 1/2001 | Lewis ....................... 73/23.34 |
| 6,186,005 | B1 * | 2/2001 | Leidl ............................ 73/597 |
| 6,293,136 | B1 | 9/2001 | Kim ........................... 73/19.03 |
| 6,314,791 | B1 | 11/2001 | Rapp et al. ................ 73/24.06 |
| 6,331,244 | B1 | 12/2001 | Lewis et al. ............. 205/777.5 |
| 6,568,271 | B1 | 5/2003 | Shah et al. .................... 73/599 |

(Continued)

FOREIGN PATENT DOCUMENTS

DE 10041921 A1 * 3/2002

OTHER PUBLICATIONS

Pohl, Alfred, "A Review of Wireless SAW Sensors", Mar. 2000, Transactions on Ultrasonics, Ferroelectrics, and Frequency Control, vol. 47, No. 2, pp. 317-332.*

(Continued)

*Primary Examiner*—Hezron Williams
*Assistant Examiner*—David A. Rogers
(74) *Attorney, Agent, or Firm*—Kermit D. Lopez; Luis M. Ortiz (57) ABSTRACT

An acoustic wave sensor apparatus is disclosed, which generally includes a piezoelectric substrate having a surface thereon. One or more interdigital transducers and a passivation layer can be formed upon the piezoelectric substrate. Additionally, an absorbent material can be formed upon the acoustic path (IDTs, electrodes, etc), such that the interdigital transducers respond to a plurality of acoustic waves propagating across the surface of the piezoelectric substrate, thereby providing data indicative of humidity in the vicinity of the piezoelectric substrate, along with the passivation layer and the interdigital transducers. Additionally, one or more heaters can be formed upon a side of the piezoelectric substrate opposite the side of the piezoelectric substrate upon which the interdigital transducers, the passivation and the absorbent material are located. The heater can be preferably configured from a material such as platinum.

17 Claims, 5 Drawing Sheets

U.S. PATENT DOCUMENTS

| | | |
|---|---|---|
| 6,607,854 B1 | 8/2003 | Rehg et al. .................... 429/13 |
| 6,640,613 B1 | 11/2003 | Rapp et al. ................ 73/24.01 |
| 6,710,515 B1 | 3/2004 | Lu et al. ..................... 310/313 |
| 6,945,090 B1 * | 9/2005 | Rodier ...................... 73/24.06 |
| 2002/0113521 A1 | 8/2002 | Rapp et al. ............. 310/313 R |
| 2003/0076743 A1 | 4/2003 | Thompson et al. ......... 367/140 |
| 2003/0124401 A1 | 7/2003 | Issacci et al. ................. 429/26 |
| 2003/0129468 A1 | 7/2003 | Issacci et al. ................. 429/34 |
| 2003/0196477 A1 | 10/2003 | Auner et al. ............... 73/24.06 |
| 2004/0244466 A1 * | 12/2004 | Shen ......................... 73/24.01 |

OTHER PUBLICATIONS

Reindl, Leonhard, "Wireless Passive SAW Identification Marks and Sensors", Jun. 2002, IEEE International Frequency Control Symposium.*

Johannes Nieβ, et al., "A miniaturized thermal desorption unit for chemical sensing below odor threshold", Sensor and Actuators, B 95 (2003), pp. 1-5.

John R. Vig, "Dual-mode Oscillators for Clocks and Sensors", 1999 IEEE Ultrasonics Symposium, pp. 859-868.

James Z. Liu, "Construction Optimization for Acoustic Wave Chemical Sensor Selectivity", (all pages), Sensor Expo Detroit, Sep. 2000.

I.D. Avramov, M. Rapp, S. Kurosawa, P. Krawczak, E. Radeva, *Gas Sensitivity Comparison of Polymer Coated SAW and STW Resonators Operating at the Same Acoustic Wave Length*, 2001 IEEE International Frequency Control Symposium and PDA Exhibition, pp. 465-473.

R.D. Hollinger, A.R. Tellakula, CT Li, V.V. Varadan, and V.K. Varadan, *Wireless Surface Acoustic Wave-Based Humidity Sensor*, SPIE vol. 3876, Sep. 1999, pp. 54-62.

D. Rebiere, C. Dejous, J. Pistre, J-F Lipsker, R. Planade, *Synthesis and Evaluation of Fluoropolyol Isomers as Saw Microsensor Coatings: Role of Humidity and Temperature*, Sensors and Actuators B49 (1998) pp. 139-145.

P. Banda, W. Wlodarski, T. Pisarkiewicz, *Theory, Design and Operation of A Conductivity Based Surface Acoustic Wave Ozone Sensor*, The 8th International Conference on Solid State Sensors and Actuators and Eurosensors IX, Jun. 1995, pp. 755-757.

W. Seidel and T. Hesjedal, *Multi-Frequency and Multi-Mode GHz Surface Acoustic Wave Sensor*, 2003 IEEE Ultrasonics Symposium.

J.W. Grate, G.C. Frye, *Acoustic Wave Sensors*, pp. 37-83.

PCT-Notification of Transmittal of The International Search Report and The Written Opinion of the International Searching Authority, or the Declaration, Date of Mailing Dec. 23, 2005.

* cited by examiner

Fig. 9

ACOUSTIC WAVE SENSOR WITH REDUCED CONDENSATION AND RECOVERY TIME

TECHNICAL FIELD

Embodiments are generally related to sensing devices, systems and methods. Embodiments are also related to acoustic wave sensors, such as, for example, surface acoustic wave (SAW) and bulk acoustic wave (BAW) devices and sensors. Embodiments are further related to humidity and condensation sensing applications.

BACKGROUND OF THE INVENTION

Acoustic wave sensors are utilized in a number of sensing applications, such as, for example, temperature, pressure, humidity and/or gas sensing devices and systems. Examples of acoustic wave sensors include devices such as acoustic wave sensors, which can be utilized to detect the presence of substances, such as chemicals and biological materials. An acoustic wave (e.g., SAW/BAW) device acting as a sensor can provide a highly sensitive detection mechanism due to the high sensitivity to surface loading and the low noise, which results from their intrinsic high Q factor.

Surface acoustic wave devices are typically fabricated using photolithographic techniques with comb-like interdigital transducers placed on a piezoelectric material. Surface acoustic wave devices may have either a delay line or a resonator configuration. The selectivity of a surface acoustic wave chemical and/or biological sensor is generally determined by a selective coating placed on the piezoelectric material. The absorption and/or adsorption of the species to be measured into the selective coating can cause mass loading, elastic, and/or viscoelastic effects on the SAW/BAW device. The change of the acoustic property due to the absorption and/or adsorption of the species can be interpreted as a delay time shift for the delay line surface acoustic wave device or a frequency shift for the resonator (BAW/SAW) acoustic wave device.

Acoustic wave sensing devices often rely on the use of quartz crystal resonator components, such as the type adapted for use with electronic oscillators. In a typical gas-sensing application, the absorption of gas molecules in a selective thin film coating (i.e., applied to one surface of the crystal) can increase the mass of the crystal, while lowering the crystal's resonant frequency. The frequency of a thickness shear mode (TSM) crystal unit, for example, such as an AT-cut unit, is inversely proportional to the thickness of the crystal plate. For example, a typical 5-MHz 3rd overtone plate is on the order of 1 million atomic layers thick. The absorption of analyte is equivalent to the mass of one atomic layer of quartz, which changes the frequency by approximately 1 ppm.

The thickness-shear-mode resonators are therefore widely referred to as a quartz crystal microbalance. Calculations have determined that the sensitivity of a fundamental mode is approximately 9 times more sensitive than that of a 3rd overtone. A 5 MHz AT-cut TSM crystal blank, for example, is approximately 0.33 mm thick (fundamental). The thickness of the electrodes can be, for example, in a range of approximately 0.2–0.5 μm. The change in frequency due to the coating is typically: $\Delta F = -2.3 \times 10^6 \, F^2 \, (\Delta M/A)$, where the value $\Delta F$ represents the change in frequency due to the coating (Hz), F represents the frequency of the quartz plate (Hz), $\Delta M$ represents the mass of deposited coating (g), and the value A represents the area coated (cm$^2$).

Selective adsorbent thin film coated acoustic sensors such as, for examples, quartz crystal resonators, surface acoustic wave and quartz crystal microbalance devices are attractive to humidity, gas and chemical detection applications because of their high sensitivity, selectivity and ruggedness. The detection mechanism implemented depends on changes in the physicochemical and electrical properties of the coated piezoelectric crystal when exposed to humidity, gas and the like. Measurement results are usually obtained as the output frequency of a loop oscillator circuit, which utilizes a coated crystal as the feedback element.

When the sensor is exposed to analytes, the thin film adsorbs the analytes, and a corresponding frequency shift is measured as a result of any physicochemical and electrical changes. Factors that contribute to the coating properties include coating density, coating modulus, substrate wetting, coating morphology, electrical conductivity, capacitance and permittivity. Coating materials selection, coating structures and coating techniques affect the sensors' responses.

Conventional techniques for thin film deposition vary extensively, depending on the properties of the coating materials and substrate. Examples of such techniques include CVD, PVD, and sol-gel for most of the inorganic and composite materials. For polymeric materials, self-assembly dipping methods, casting, spray coating, and/or spin coating from a solution of the polymer in a volatile solvent are often preferred. Configurations based on these conventional techniques generally determine the properties of an acoustic wave sensor. Coating methods are also important for a sensor's repeatability. Because of their relatively short lifetimes, such sensors are replaced more often than those based on metal oxide. When sensors are replaced, they lose their memory of previously learned odors. In other words, the response curves of such devices vary, and the replacement sensors must then be retrained and/or recalibrated.

For practical reasons, zeolites are widely utilized as the physi-sorption coating materials. Zeolites are crystalline alumino-silicates of alkali or alkaline earth elements (e.g., Li, Na, K, Mg, Ca, Ba) with frameworks based on extensive 3-dimentional networks of $AlO_4$ and $SO_4$ tetrahedra. These tetrahedra are assembled into secondary polyhedral building blocks such as cubes, octahedral and hexagonal prisms. The final zeolite structure consists of assemblages of the secondary blocks into a regular, 3-dimentional crystalline framework. Each aluminum atom, for example, possesses a (−1) charge and this gives rise to an anionic charge in the network.

Cations are necessary to balance the charge and occupy non-framework positions. Typically the framework is composed of a regular structure of interconnected cages and/or channels. These devices or systems of essentially "empty" cages and/or channels provide the high storage capacities necessary for good adsorbents. Zeolite adsorbents are characterized by their uniform intra-crystalline aperture sizes. The uniformly sized apertures enable molecular discrimination on the basis of size (e.g., steric separation). Molecules larger than the maximum size that can diffuse into the crystal are excluded.

The sorption capacity and selectivity can be significantly affected by the type of cation used and the extent of ion exchange. This type of modification is important in optimizing zeolites for gas separation. The uniform pore structure, ease of aperture size modification, excellent thermal and hydrothermal stability, high sorption capacity at low partial pressures, and modest cost have made zeolites widely used in many separation application. For example, a selective adsorbent thin film coated quartz crystal microbalance chemical sensor can be utilized for the selective detection of CO. The thin coating comprises a solid non-porous inorganic matrix and porous zeolite crystals contained within the inorganic matrix, the pores of the zeolite crystals selectively adsorb chemical entities of a size less than a preselected magnitude.

The matrix can be selected from the group of sol-gel derived glasses, polymers and clay. The pores of the zeolite crystals are modified so as to be Lewis or Bronsted acidic or basic and capable of providing intrazeolite ligation by the presence of metal ions. The film can be configured from an alumina, boro-alumino-silicate, titanium, hydrolyzed diethoxydiphenyl silane, or silane rubber matrix containing zeolite crystals. The thickness of the inorganic matrix is generally about 0.001–10 µm and the diameter of the pores of the zeolite crystals is approximately 0.25–1.2 nm. The coating is a single layer of zeolite crystals protruding from an amorphous $SiO_2$ matrix.

A polymer can be defined as a compound consisting of a large number of repeating units, called monomers. These monomers are joined together by covalent bonds to form a long chain. The degree of polymerization is defined as the number of repeating units in the chain. The properties of the polymer depend on the overall size of the polymer chain and on the inter- and intra-molecular forces that hold the polymer together. In general, the polymer properties of interest can be characterized as diffusion/permeation properties or as mechanical properties. The measurement of diffusion/permeation properties is straightforward when diffusion of a species into a polymer film produces a simple mass-loading effect. Polymers used as sensor coatings are butyl rubber, cellulose polymers, polysiloxanes, polyaniline and polyethylene, and the like.

Polymers, specifically rubbery, amorphous polymers, have several inherent advantages as chemically sensitive sensor coatings. They can be deposited as thin, adherent, continuous films of fairly uniform thickness by solvent casting or spray coating. They are nonvolatile and of homogeneous composition, and their chemical and physical properties can be modified to some extent by judicious choice of monomers and synthetic procedures. The glass transition temperature Tg is the temperature at which a polymer changes from glassy to rubbery. Above Tg, permeability is governed entirely by diffusion forces and adsorption proceeds rapidly and reversibly. One more advantage of rubbery, amorphous polymers is that their sorption isotherms are often linear over relatively large ranges in penetrant concentration.

One of the disadvantages with polymers, however, such as a polyimide film used in most humidity sensors, is that repeated heating can delaminate the polymer or polyimide film due to thermal expansion coefficient mismatch with the substrate and absorption in general. Heating therefore can cause irreversible change to the polyimide film. In high condensing applications (e.g., a fuel cell), a sensor that relies upon a polymer or polyimide film cannot meet these requirements.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide improved sensor methods and systems.

It is another aspect of the present invention to provide for improved acoustic wave sensor methods and systems.

It is yet a further aspect of the present invention to provide an improved multiple mode surface acoustic wave (SAW) or bulk acoustic wave (BAW) sensing system.

It is also an aspect of the present invention to provide for an improved humidity and/or condensation sensor.

The aforementioned aspects of the invention and other objectives and advantages can now be achieved as described herein. An acoustic wave sensor apparatus is disclosed, including a system and method thereof. Such an apparatus generally includes a piezoelectric substrate having a surface thereon. One or more interdigital transducers and a passivation layer can be formed upon the piezoelectric substrate. Additionally, an absorbent material can be formed upon the passivation layer, such that interdigital transducers respond to a plurality of acoustic waves propagating across the surface of the piezoelectric substrate, thereby providing data indicative of humidity in the vicinity of the piezoelectric substrate, along with the passivation layer and the interdigital transducers. Additionally, one or more heaters can be formed upon a side of the piezoelectric substrate opposite the side of the piezoelectric substrate upon which the interdigital transducers, the passivation and the absorbent material are located. The heater can be preferably configured from a material such as platinum.

The plurality of acoustic waves propagating across the surface of the piezoelectric substrate comprise multiple mode frequency outputs, wherein at least one frequency mode thereof can be optimized while all remaining frequency modes among the multiple mode frequency outputs are suppressed in order to generate particular data indicative of a monitored chemical species (e.g., humidity). The plezoelectric substrate can vibrate in the optimized frequency mode when condensation occurs in a vicinity of the piezoelectric substrate, such that the condensation acts as a damping force thereon. The piezoelectric substrate generally vibrates in a shear horizontal direction in order to lessen damping thereof.

Additionally, a plurality of oscillators can be provided, which are associated with the interdigital transducers, such that each sensing component of the plurality of sensing components is located in a feedback loop with an oscillator of the plurality of oscillators to thereby provide a multiple mode acoustic wave sensor that provides multiple mode frequency outputs thereof. Such multiple modes frequency outputs can comprise at least one of the following types of data: flexural plate mode (FMP) data, acoustic plate mode data, shear-horizontal acoustic plate mode (SH-APM) data, amplitude plate mode (APM) data, thickness shear mode (TSM) data, surface acoustic wave mode (SAW), bulk acoustic wave mode (BAW) data, torsional mode data, love wave data, leaky surface acoustic wave mode (LSAW) data, and pseudo surface acoustic wave mode (PSAW) data, at least one multiple mode acoustical vibration amplitude, transverse mode data, surface-skimming mode data, surface transverse mode data, harmonic mode data, and overtone mode data. Generally, the multiple mode acoustical vibration amplitude can be controlled by such oscillators.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1 illustrates a perspective view of an interdigital surface wave device, which can be adapted for use with one embodiment.

DETAILED DESCRIPTION OF THE INVENTION

The particular values and configurations discussed in these non-limiting examples can be varied and are cited merely to illustrate at least one embodiment and are not intended to limit the scope of the invention.

Many modes of vibrations can exist in an acoustic wave device. Acoustic wave devices are typically designed such that only one mode of vibration is optimized, while other modes are suppressed. Such "undesired" mode(s), however, can be utilized for desorption in affinity/adsorption type sensors. Such modes can include, for example, flexural plate mode (FPM), acoustic plate mode, shear-horizontal acoustic plate mode (SH-APM), amplitude plate mode (APM), thickness shear mode (TSM), surface acoustic wave mode (SAW), bulk acoustic wave mode (BAW), Torsional mode, love wave, leaky surface acoustic wave mode (LSAW), pseudo surface acoustic wave mode (PSAW), transverse mode, surface-skimming mode, surface transverse mode, harmonic modes, and/or overtone modes. Thus, in accordance with embodiments disclosed herein, multiple vibration modes can be utilized to produce a multiple mode acoustic wave device, particularly one that is utilized for humidity and/or condensation sensing.

Figure 1:
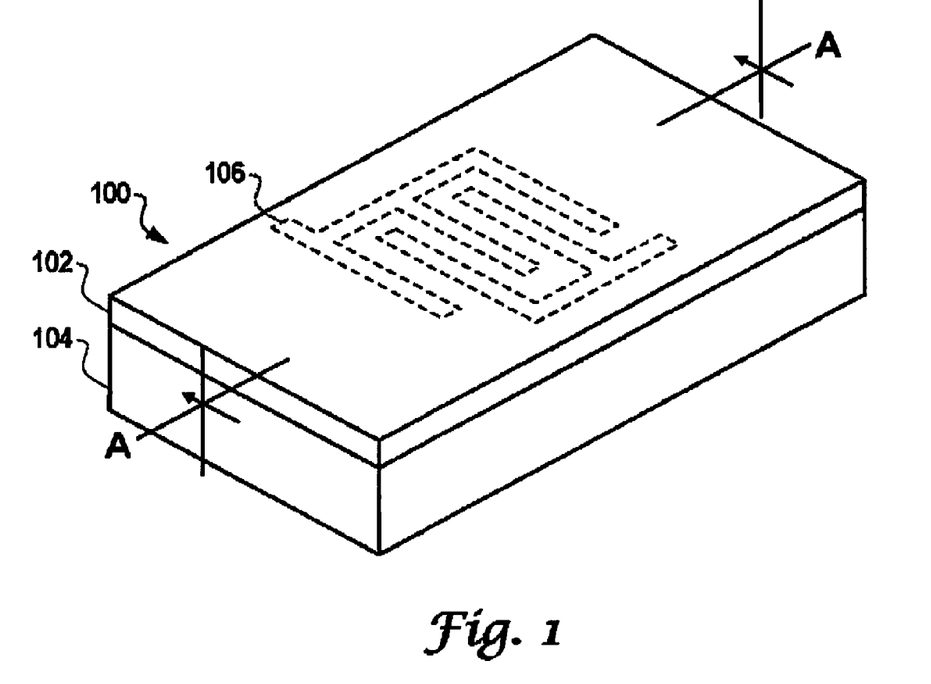

FIG. 1 illustrates a perspective view of an interdigital surface wave device 100, which can be implemented in accordance with one embodiment. Surface wave device 100 can be adapted for use in humidity sensing activities, as described in further detail herein. Surface wave device 100 can be configured to generally include an interdigital transducer 106 formed on a piezoelectric substrate 104. The surface wave device 100 can be implemented in the context of a sensor chip. Interdigital transducer 106 can be configured in the form of an electrode.

Figure 2:
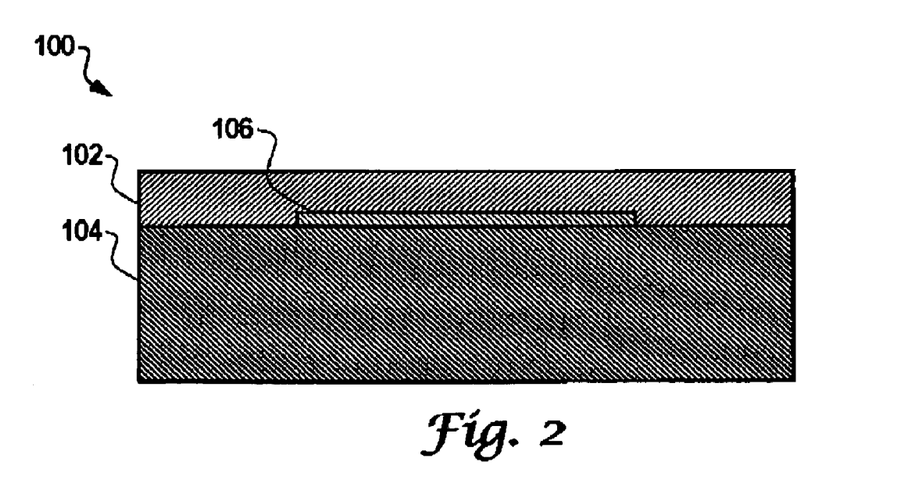
FIG. 2 illustrates a cross-sectional view along line A—A of the interdigital surface wave device depicted in FIG. 1, which can be adapted for use with one embodiment.

FIG. 2 illustrates a cross-sectional view along line A—A of the interdigital surface wave device 100 depicted in FIG. 1, in accordance with one embodiment. Piezoelectric substrate 104 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few.

Interdigital transducer 106 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAI. Third, interdigital transducer 106 can be formed from metal-nonmetal compounds (e.g., ceramic electrodes based on TiN, $CoSi_2$, or WC). Depending on the biocompatibility of the substrate and interdigital transducer materials, a thin layer of biocompatible coating 102 may be used to cover the interdigital transducer and the substrate.

Figure 3:
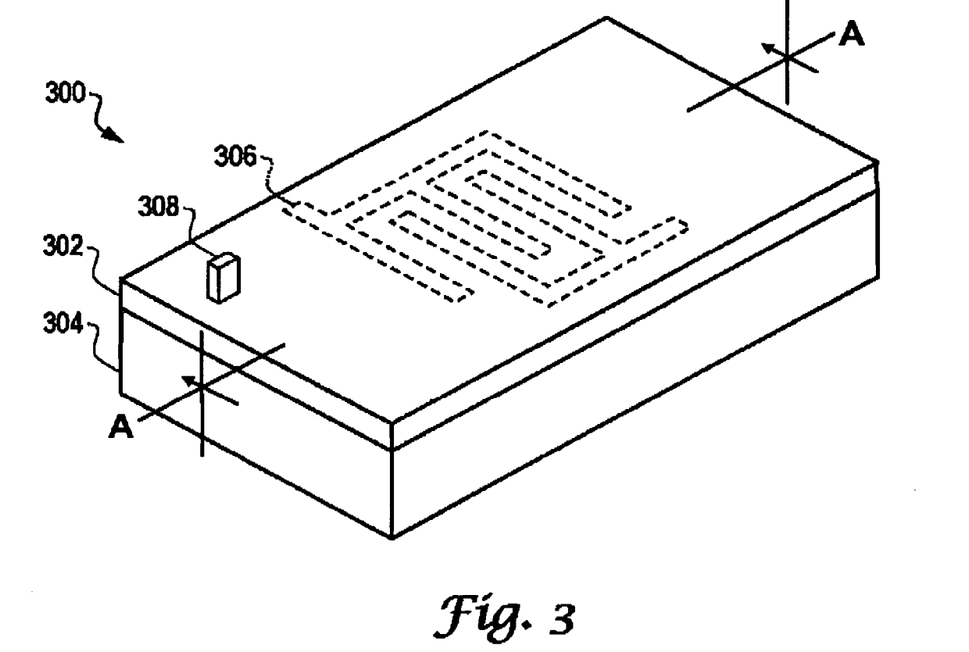
FIG. 3 illustrates a perspective view of an interdigital surface wave device, which can be adapted for use with one embodiment.
Figure 4:
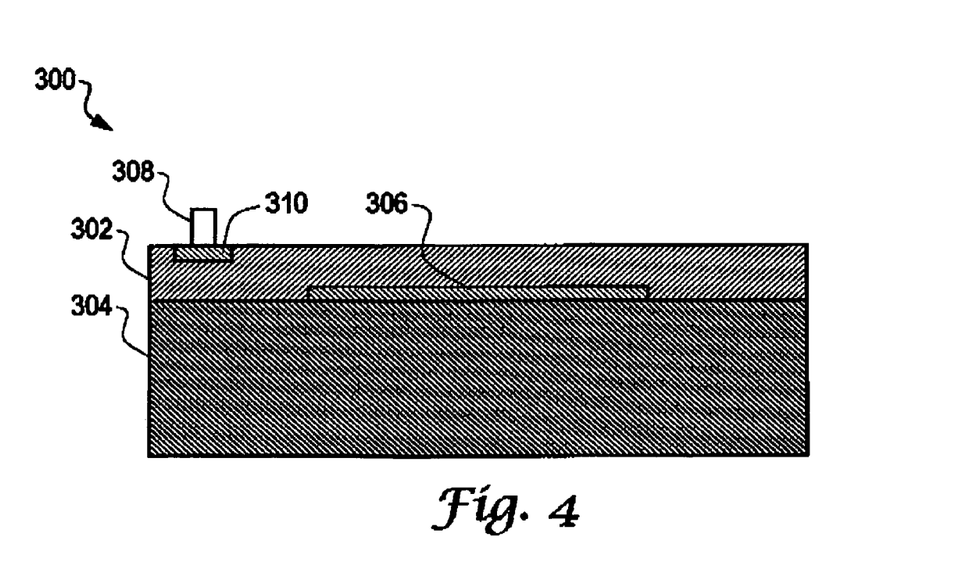
FIG. 4 illustrates a cross-sectional view along line A—A of the interdigital surface wave device depicted in FIG. 3, which can be adapted for use with one embodiment.

FIG. 3 illustrates a perspective view of an rnterdigital surface wave device 300, which can be implemented in accordance with an alternative embodiment. The configuration depicted in FIGS. 3–4 is similar to that illustrated in FIGS. 1–2, with the addition of an antenna 308, which is connected to and disposed above a wireless excitation component 310 (i.e., shown in FIG. 4). Surface wave device 300 generally includes an interdigital transducer 306 formed on a piezoelectric substrate 304. Surface wave device 300 can therefore function as an interdigital surface wave device, and one, in particular, which utilizes surface-skimming bulk wave techniques. Interdigital transducer 306 can be configured in the form of an electrode. A coating 302 can be selected which withstands the detrimental effects of repeated heating.

A change in acoustic properties can be detected and utilized to identify or detect the substance (e.g., humidity/condensation) or species absorbed and/or adsorbed by the interdigital transducer 306. Thus, interdigital transducer 306 can be excited via wireless means to implement a surface acoustical model. Thus, antenna 308 and wireless excitation component 310 can be utilized to excite one or more frequency modes associated with the flow of a fluid for fluid flow analysis thereof.

FIG. 4 illustrates a cross-sectional view along line A—A of the interdigital surface wave device 300 depicted in FIG. 3, in accordance with one embodiment. Thus, antenna 308 is shown in FIG. 4 disposed above coating 302 and connected to wireless excitation component 310, which can be formed within an area of coating 302. Similar to the configuration of FIG. 2, Piezoelectric substrate 304 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few.

Interdigital transducer 306 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAI. Third, interdigital transducer 306 can be formed from metal-nonmetal compounds (e.g., ceramic electrodes based on TiN, $CoSi_2$, or WC).

Figure 5:
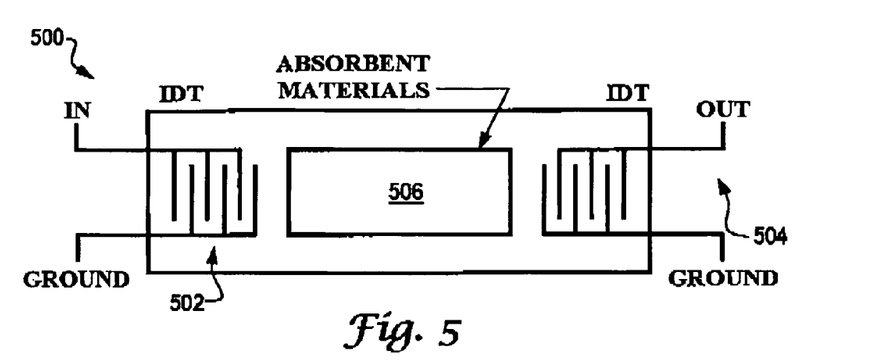
FIG. 5 illustrates a top view of an acoustic wave sensor apparatus, which can be implemented in accordance with a preferred embodiment.
Figure 6:
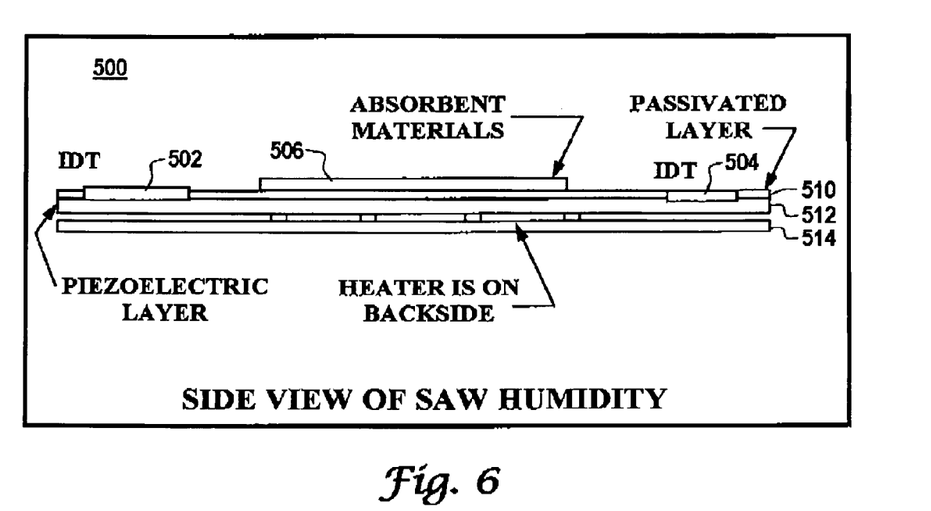
FIG. 6 a side sectional view of the acoustic wave sensor apparatus depicted in FIG. 5, in accordance with a preferred embodiment.

FIG. 5 illustrates a top view of an acoustic wave sensor apparatus 500, which can be implemented in accordance with a preferred embodiment. FIG. 6 a side sectional view of the acoustic wave sensor apparatus 500 depicted in FIG. 5. In FIGS. 5–6, identical or similar parts or elements are generally indicated by identical reference numerals. Apparatus 500 generally includes a piezoelectric substrate 512 having a surface thereon. One or more interdigital transducers 502, 504 can be formed upon piezoelectric substrate 512. Note that each interdigital transducer 502, 504 are analogous to interdigital transducer 106 depicted in FIG. 1. A passivation layer 510 can also be formed upon piezoelectric substrate 512. An absorbent material 506 can then be formed upon passivation layer 510. The interdigital transducers 502, 504 can respond to a plurality of acoustic waves propagating across the surface of piezoelectric substrate 512, thereby provide data indicative of humidity in the vicinity of piezoelectric substrate 512, passivation layer 510 and interdigital transducer 502, 504.

Additionally, one or more heaters, such as heater 514 can be located upon the side (i.e., backside) of piezoelectric substrate 512 that is opposite the side upon which interdigital transducer 502, 504, passivation layer 510 and the absorbent material 506 are located. Heater 514 prevents delamination of polyimide film due to thermal expansion coefficient mismatch with the piezoelectric substrate 512 and absorption in nature. Heater 514 thus can prevent irreversible change to the film. Such film may be a polyimide integrated with heater 514 on substrate 512.

Apparatus 500 functions as a humidity sensor and can use humidity absorbent/adsorbent materials in order to implement absorbent material 506. Thus, absorbent material 506 can be formed from material such as, for example, cellulose acetate (CAB); polyimide, polyphenol resin (PPR), NAFION, Silica ($SiO_2$), Alpha-alumina ($Al_2O_3$), Glass-fiber resins, Organic-inorganic ($AMPS/SiO_2$hybrid, Ionenes, and/or $Li_2SnO_3$. For most applications, the envimnmental conditions dictate the sensor/sensing materials choice. In high condensing applications such as fuel cells, the humidity sensing materials (e.g., absorbent material 506) could be Silica ($SiO_2$), Alpha-alumina ($Al_2O_3$), zeolite and $Li_2SnO_3$, and the like. In accordance with a preferred embodiment, the sensing materials (e.g., absorbent material 506) can be formed from a porous ceramic or a similar material.

The surface acoustic wave sensor apparatus 500 described herein can employ higher vibrational amplitudes for desorption purposes than conventional sensor devices. Higher amplitudes require higher drive levels, i.e., high currents through the quartz crystals from which piezoelectric substrate 512 may be configured. The desorption is generally due to the combined effects from high amplitude vibration and heat generated by the surface acoustic wave sensor apparatus 500 itself. The use of high amplitude fundamental, along with high amplitude overtones can be controlled and programmed through oscillators and associated electronics. An example of such oscillators and associated electronics are described herein with respect to FIG. 7 (e.g., see acoustic wave sensor apparatus 700).

As indicated earlier, many modes can exist in an acoustic wave device. Multiple modes can be optimized, while other modes may be suppressed, depending upon design considerations. Multiple modes can be optimized, for example, by designing the parameters (e.g., the electrode thickness of interdigital transducers 502, 504, the "aperture" size of interdigital transducers 502, 504, electrode materials selections, less number of IDT fingers, etc.) at the verge of 2 modes or 3 modes. Conventional acoustic devices are designed away from such areas, which are not taken into consideration in sensing applications.

A SAW device such as surface acoustic wave sensor apparatus 500 can be excited to vibrate in the surface mode first, when condensation occurs, such that the water on the surface of the SAW device acts as a damping force for the device. Because the device is designed to be able to vibrate at a shear horizontal direction also, there will be much less damping, so that the vibration would be changed to a shear horizontal direction and the SAW device could also function as an SH-SAW. Through prudent design, the same sensing layer can also function as a wave guide.

The change in the frequency of a quartz crystal unit with respect to the change in amplitude of the drive level can be referred to as the amplitude-frequency effect. A resulting data curve can be obtained in stable dry ambient conditions. In reality, however, the total frequency shift can be from the amplitude change (e.g., a base line), temperature (compensated) and the desorption of the analyte(s).

Figure 7:
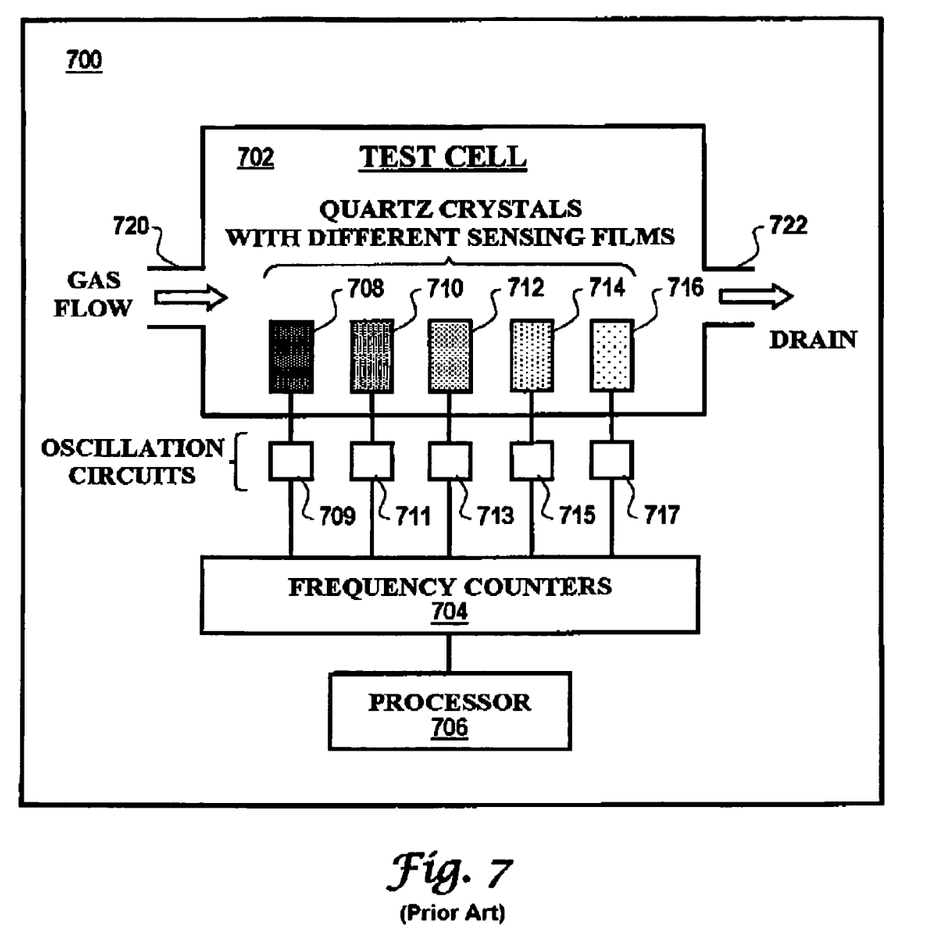
FIG. 7 illustrates a block diagram of a multiple modes acoustic wave sensor system, which can be adapted for use in accordance with an embodiment.

FIG. 7 illustrates a block diagram of an acoustic wave sensor apparatus 700, which can be adapted for use in accordance with an embodiment. Apparatus 700 can be implemented as an array of sensors, such as, for example, a plurality of quartz crystals 708, 710, 712, 714, and 716, which are located within a test cell 702. Each quartz crystal can be placed in a feedback path of an oscillator. For example, quartz crystal 708 can be placed in a feedback path of oscillator circuit 709, while quartz crystal 710 is generally placed in the feedback path of oscillator circuit 711. Similarly, quartz crystal 712 can be place in the feedback path of oscillator circuit 713, while quartz crystal 714 is generally placed in the feedback path of oscillator circuit 715. Finally, quartz crystal 716 is generally placed in the feedback path of oscillator circuit 717. Oscillator circuits 709, 711, 713, 715 and 717 communicate with frequency counter 704, which in turn is under the command of a processor 706. In practice, gas flow or another chemical flow can enter test cell 702 through an entrance 720 and exist via a drain 722.

In terms of coating selection for an array of sensors, such as apparatus 700 depicted in FIG. 7, a minimum number of sensor/coatings can be implemented, in order to adequately represent the data. Thus, coatings exhibiting similar or redundant response should be eliminated. A coating, when selected from a group of coatings, should be based on considerations such as sensitivity, stability or cost.

The selectivity of a humidity sensor can be improved by taking advantage of selective adsorbent materials. Some improvement can be achieved by utilizing selective permeable filters. Interferences, however, may not always be known before the use of sensor. In addition, applications that require simultaneous monitoring for multiple analytes require multiple sensors. In such cases, the use of arrays of sensors, each bearing a coating with a different degree of selectivity for the analytes of interest, can be utilized.

In terms of pattern-recognition analysis, a coating can be classified according to its response to a set of analytes. Each sensor in an array can be designed with a different coating, wherein each coating is selected to respond differently to the members of a set of analytes. The combination of responses should produce a unique fingerprint for each analyte. A number of methods have been developed for establishing correlations between the pattern of responses from an array of chemical sensors and identity of the corresponding analyte. The efficiency of the array depends on the uniqueness of the coating responses.

Figure 8:
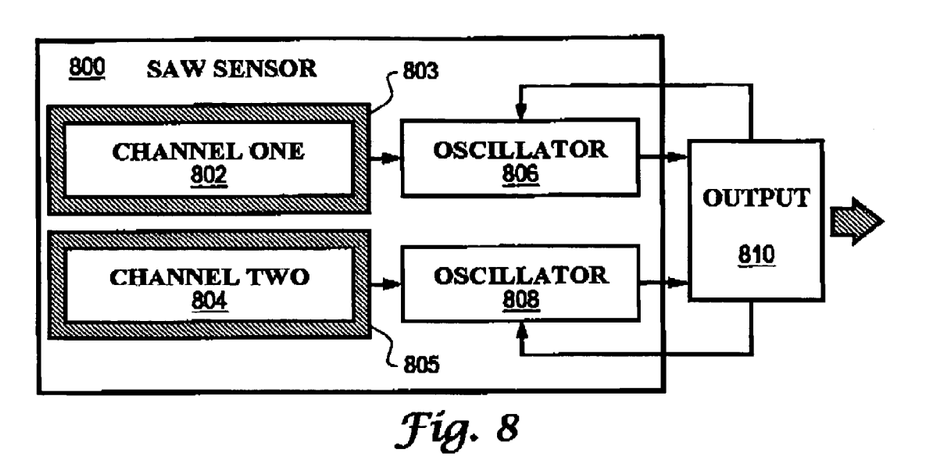
FIG. 8 illustrates a block diagram of a multiple mode acoustic wave sensor system, which can be implemented in accordance with an embodiment.

FIG. 8 illustrates a block diagram of a multiple mode acoustic wave sensor apparatus 800, which can be adapted for use in humidity sensing applications in accordance with an embodiment. Apparatus 800 can be implemented as a two-channel SAW sensor, composed of a first channel 802 and a second channel 804. First channel 802 is composed of a sensing coating 803, while second channel 804 includes a sensing coating 805. Each channel 802 and 804 can include a quartz crystal sensing component. Second channel 804 includes a quartz crystal structure, which is identical to that contained by first channel 802, except for the sensing coatings 803 and 805. The two channels 802 and 804 can be placed in the feedback path of two identical oscillators 806 and 808, and the output 810 of the circuit is the difference of the two frequencies produced thereof. With this arrangement, the SAW sensor apparatus 800 can increase the sensing accuracy by eliminating response due to changes in the environment other than the monitored chemical species.

In accordance with another embodiment, however, SAW sensor apparatus 800 can be implemented as a SAW/BAW humidity/dew point sensor.

Frequency can be measured with far higher accuracy than any other quantity. Dual modes excitation, such as that provided by apparatus 800, can provide superior sensing because the two modes occupy the same volume of quartz. In multiple mode excitation, the multiple excited modes occupy the same volume of piezoelectric material. Multiple modes can be excited simultaneously by means of multiple oscillator circuits sharing a common piezoelectric device. Humidity tends to condense at the surface of sensing materials. The use of multiple modes can therefore shake away the water droplet and the sensor will recover quickly from water saturation. In this design, however, other modes are designed to be excited after the sensor's exposure to the analyte(s).

The piezoelectric substrate materials could be α-quartz, lithium niobate ($LiNbO_3$), and lithium tantalate ($LiTaO_3$) as well as $Li_2B_4O_7$, $AlPO_4$, . . . $GaPO_4$, langasite ($La_3Ga_5SiO_{14}$), ZnO, and epitaxially grown (Al, Ga, In) nitrides. The electrode material for the piezoelectric device could be divided into three groups: metals (e. g. Al, Pt, Au, Rh, Ir, Cu, Ti, W, Cr, and Ni), alloys (e. g. NiCr, CuAl) and metal-nonmetal compounds (e. g. ceramic electrodes: TiN, $CoSi_2$, and WC).

Selective adsorbent coating materials have been used for different gaseous detection applications. Examples of such coating materials include $NO_2$, $SO_2$, $CO_2$, $H_2S$, $NH_3HCl$, water vapor and hydrocarbons. Adsorption occurs due to molecular interactions between the adsorbing species and the solid. Chemisorption occurs when strong interactions, including hydrogen bonding and covalent and ionic bond formation. Chemisorption occurs even at very low concentrations, and the chemisorption species are often "irreversibly" bound to the surface. In other words, they will not readily desorb under ambient temperature conditions.

Physical adsorption represents a weak interaction, typically van der Waals forces. Common materials for physical sorption can include, for example, activated charcoal, silica and alumina gels, and zeolites, porous polymers (e.g., TENAX, XAD, and CHROMOSORB). Adsorbents tend to be micro-porous solids possessing large surface areas (e.g., 200 to 1000 $m^2/g$). A high degree of discrimination is achieved by the use of size specific materials, having a controlled pore size just larger than the kinetic diameter of the desired analyte. This excludes all larger species from the pores entirely; molecules significantly smaller than the chosen analyte, though able to fit into the pores, have a smaller interaction energy due to the size mismatch.

Vibrations of acoustic wave devices could be used to break down the bonding (i.e., connections) between the analytes(s) and the sensing materials. A variety of acoustic modes may propagate in a piezoelectric devlce; this includes bulk waves and surface waves. For most acoustic wave devices the substrate materials and crystal orientation are usually chosen such that only one mode can be excited. However, other modes could be excited. The vibrational frequencies and amplitudes can be chosen, such that they are most suitable for breaking the bonding between the sensing materials and analyte(s). The acoustic wave device/sensor disclosed herein is therefore capable of detecting condensation on its surface. Such a sensor system or device can be designed such that when condensation occurs, the oscillator (s) operate at higher amplitudes, hence the vibration and heat generated through this process will be able to get rid of the water condensed on the sensing surface.

Figure 9:
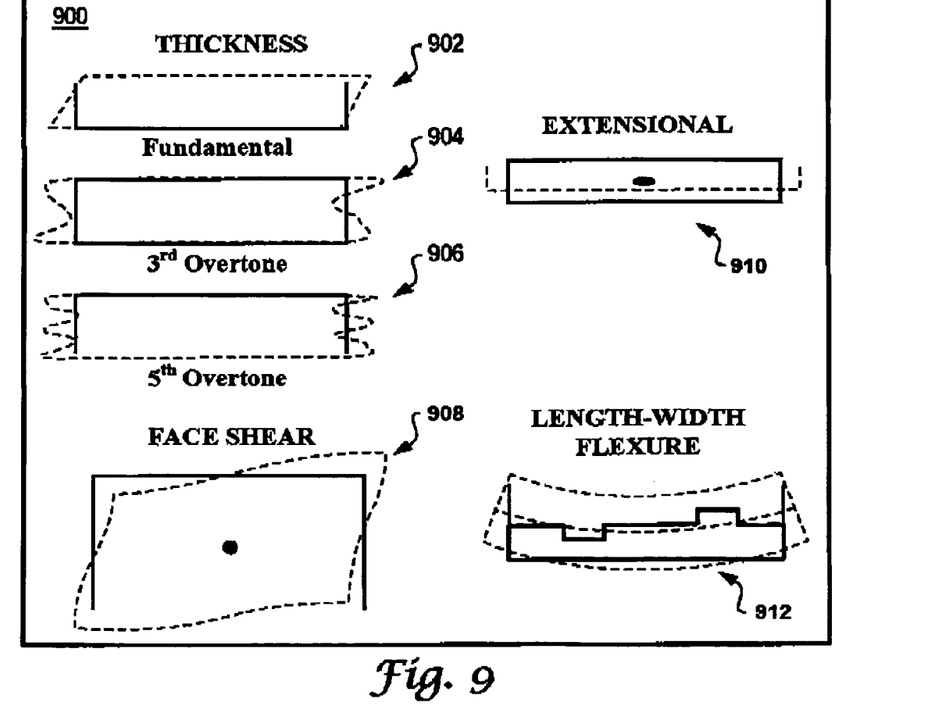
FIG. 9 illustrates a diagram depicting varying modes, which can be utilized for desorption in a humidity sensor configuration, in accordance with preferred or alternative embodiments of the present invention

FIG. 9 illustrates a diagram depicting varying modes 900, which can be utilized for desorption in affinity/adsorption type sensors, in accordance with preferred or alternative embodiments of the present invention. For example, "thickness" is depicted in FIG. 9, including a fundamental 902, $3^{rd}$ overtone 904 and $5^{th}$ overtone 906. A face shear 908 is also depicted in FIG. 9, along with an extensional 910 and a length-width fiexure 912. FIG. 9 illustrates the fact that many modes of vibrations can exist in an acoustic wave device, and that acoustic wave and/or BAW devices are typically designed such that only one mode of vibration is optimized, while other modes are suppressed.

According to the embodiments described herein, such "undesired" mode(s), can be utilized for desorption in affinity/adsorption type sensors. Such modes can include, for example, flexural plate mode (FPM) (e.g., see length-width flexure 912), shear-horizontal acoustic plate mode (SH-APM) (e.g., see face shear 908), and thickness shear mode (TSM) (e.g., see fundamental 902, $3^{rd}$ overtone 904 and $5^{th}$ overtone 906). It can be appreciated of course that such modes are only a few of many other types of modes which can be utilized in accordance with preferred or alternative embodiments, and are referred to herein for illustrative purposes only.

The humidity sensor embodiments described herein can be applied to a number of important industrial and commercial devices and systems. One significant application of the sensors disclosed herein involves fuel cell applications. There are several kinds of fuel cells, but Polymer Electrolyte Membrane (PEM) fuel cells-also called Proton Exchange Membrane fuel cells-are the type typically used in automobiles. A PEM fuel cell uses hydrogen fuel and oxygen from the air to produce electricity. In general, most fuel cells designed for use in vehicles produce less than 1.16 volts of electricity, which is usually not sufficient to power a vehicle. Therefore, multiple cells must be assembled into a fuel cell stack. The potential power generated by a fuel cell stack depends on the number and size of the individual fuel cells that comprise the stack and the surface area of the PEM.

One example of a fuel cell application in which one or more of the methods and systems disclosed herein can be implemented is disclosed in U.S. Pat. No. 6,607,854, "Three-Wheel Air Turbocompressor for PEM fuel Cell Systems," and issued to Rehg et al. on Aug. 19, 2003. U.S. Pat. No. 6,607,854 discloses a fuel cell system comprising a compressor and a fuel processor downstream of the compressor. In U.S. Pat. No. 6,607,854, a fuel cell stack is configured in communication with the fuel processor and compressor. A combustor is downstream of the fuel cell stack. First and second turbines are downstream of the fuel processor and in parallel flow communication with one another. A distribution valve is in communication with the first and second turbines. The first and second turbines are mechanically engaged to the compressor. A bypass valve is intermediate the compressor and the second turbine, with the bypass valve enabling a compressed gas from the compressor to bypass the fuel processor. U.S. Pat. No. 6,607,854 is assigned to Honeywell International, Inc., and is incorporated herein by reference.

Another example of a fuel cell application in which one or more of the methods and systems disclosed herein can be implemented is disclosed in U.S. Patent Publication No. 2003/0129468A1, "Gas Block Mechanism for Water Removal in Fuel Cells" to Issacci et al., which was published on Jul. 10, 2003 and is assigned to Honeywell International, Inc. U.S. Patent Publication No. 2003/0129468A1 is incorporated herein by reference. A further example of a fuel cell application in which one or more of the methods and systems disclosed herein can be implemented is disclosed in U.S. Patent Publication No. 2003/0124401A1, "Integrated Recuperation Loop in Fuel Cell Stack" to Issacci et al., which was published on Jul. 3, 2003 and is assigned to Honeywell International, Inc. U.S. Patent Publication No. 2003/0124401A1 is also incorporated herein by reference.

It is important to note that when a SAW device operates at a higher temperature or at a higher vibration amplitude, the SAW device may suffer from stress-induced materials transport, (Acousto-migration) i.e., the IDT finger electrodes or piezoelectric substrate may be damaged by cracking, etc. Research has shown that SAW filters for high power applications typically use copper electrode instead of aluminum or its alloy. The high diffusivity and the oxidation behavior of copper, however, require a surrounding thin barrier layer, which can be particularly efficient against copper and oxygen diffusion. TaSiN can therefore be utilized for such a purpose.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The invention claimed is:

1. An acoustic wave sensor apparatus, comprising:
a plezoelectric substrate having a surface thereon;
at least one interdigital transducer and a passivation layer formed upon said piezoelectric substrate;
an absorbent material formed upon said passivation layer, wherein said at least one interdigital transducer responds to a plurality of acoustic waves propagating across said surface of said piezoelectric substrate, wherein said plurality of acoustic waves propagating across said surface of said piezoelectric substrate comprise multiple mode frequency outputs, such that a plurality of frequency modes thereof are optimized while all remaining frequency modes among said multiple mode frequency outputs are suppressed in order to generate particular data indicative of a monitored chemical species in vicinity of said piezoelectric substrate, said passivation layer and said at least one interdigital transducer.

2. The apparatus of claim 1 further comprising at least one heater formed upon a side of said piezoelectric substrate opposite a side upon which said at least one inter-digital transducer, said passivation and said absorbent material are located.

3. The apparatus of claim 2 wherein said at least one heater comprises platinum.

4. The apparatus of claim 1 wherein said piezoelectric substrate vibrates in said at least one frequency mode when condensation occurs in a vicinity of said piezoelectric substrate, such that said condensation acts as a damping force thereon.

5. The apparatus of claim 4 wherein said piezoelectric substrate vibrates in a shear horizontal direction in order to lessen damping thereof.

6. The apparatus of claim 1 further comprising:
a plurality of oscillators associated with said at least one interdigital transducer;
plurality of sensing components is located in a feedback loop with an oscillator of said plurality of oscillators to thereby provide a multiple mode acoustic wave sensor that provides multiple mode frequency outputs thereof.

7. The apparatus of claim 6 wherein said multiple modes frequency outputs comprise at least one of the following types of data: flexural plate mode (FMP) data, acoustic plate mode data, and shear-horizontal acoustic plate mode (SH-APM) data.

8. The apparatus of claim 7 wherein said multiple mode frequency outputs further comprises at least one of the following types of data: amplitude plate mode (APM) data, thickness shear mode (TSM) data, surface acoustic wave mode (SAW), and bulk acoustic wave mode (BAW) data.

9. The apparatus of claim 8 wherein said multiple mode frequency outputs further comprises at least one of the following types of data: torsional mode data, love wave data, leaky surface acoustic wave mode (LSAW) data, and pseudo surface acoustic wave mode (PSAW) data, and at least one multiple mode acoustical vibration amplitude.

10. The apparatus of claim 9 wherein said multiple mode frequency outputs further comprises at least one of the following types of data: transverse mode data, surface-skimming mode data, surface transverse mode data, harmonic mode data, and overtone mode data.

11. The apparatus of claim 10 wherein said at least one multiple mode acoustical vibration amplitude is controlled by said plurality of oscillators.

12. An acoustic wave sensor apparatus, comprising:
a piezoelectric substrate having a surface thereon;
at least one interdigital transducer and a passivation layer formed upon said piezoelectric substrate;
an absorbent material formed upon said passivation layer, wherein said at least on interdigital transducer responds to a plurality of acoustic waves propagating across said surface of said piezoelectric substrate, that provide data indicative of a monitored chemical species in a vicinity of said piezoelectric substrate, said passivation layer and said at least on interdigital transducer;

at least one heater formed upon a side of said piezoelectric substrate opposite a side upon which said at least one interdigital transducer, said passivation and said absorbent material are located;

a plurality of oscillators associated with said at least one interdigital transducer; and a plurality of sensing components is located in a feedback loop with an oscillator of said plurality of oscillators to thereby provide a multiple mode acoustic wave sensor that provides multiple mode frequency outputs thereof, wherein said at least one multiple mode acoustical vibration amplitude is controlled by said plurality of oscillators.

13. The apparatus of claim 12 wherein said piezoelectric substrate vibrates in at least one frequency mode among said multiple mode frequency outputs when condensation occurs in a vicinity of said piezoelectric substrate, such that said condensation acts as a damping force thereon.

14. The apparatus of claim 13 wherein said piezoelectric substrate vibrates in a shear horizontal direction in order to lessen damping thereof.

15. A method for multiple mode acoustic wave sensing, comprising the steps of:

providing a piezoelectric substrate having a surface thereon;

forming at least one interdigital transducer and a passivation layer upon said piezoelectric substrate; and forming an absorbent material upon said passivation layer, wherein said at least one interdigital transducer responds to a plurality of acoustic waves propagating across said surface of said piezoelectric substrate; and configuring said piezoelectric substrate such that said plurality of acoustic waves propagating across said surface of said piezoelectric substrate comprise multiple mode frequency outputs, wherein a plurality of frequency modes thereof is optimized while all remaining frequency modes among said multiple mode frequency outputs are suppressed in order to generate particular data indicative of a monitored chemical species in a vicinity of said piezoelectric substrate, said passivation layer and said at least on interdigital transducer.

16. The method of claim 15 further comprising the step of forming at least one heater formed upon a side of said plezoelectric substrate opposite a side upon which said at least one interdigital transducer, said passivation and said absorbent material are located.

17. The method of claim 16 further comprising the step of configuring said piezoelectric substrate to vibrate in said at least one frequency mode when condensation occurs in a vicinity of said piezoelectric substrate, such that said condensation acts as a damping force thereon.

* * * * *